United States Patent [19]

Horodysky et al.

[11] Patent Number: 4,522,734
[45] Date of Patent: Jun. 11, 1985

[54] BORATED FRICTION REDUCING ADDITIVES AND COMPOSITIONS THEREOF

[75] Inventors: Andrew G. Horodysky, Cherry Hill; Henry Ashjian, East Brunswick; Henry A. Gawel, Clark, all of N.J.

[73] Assignee: Mobil Oil Corporation, New York, N.Y.

[21] Appl. No.: 436,752

[22] Filed: Oct. 25, 1982

[51] Int. Cl.$^3$ ............................................. C10M 1/54
[52] U.S. Cl. ................................. 252/49.6; 549/213; 260/462 R; 260/462 C; 252/52 A
[58] Field of Search ................... 252/49.6, 52 A, 49.7; 549/213; 260/462 R, 462 C

[56] References Cited

U.S. PATENT DOCUMENTS

| | | | |
|---|---|---|---|
| 2,611,745 | 9/1952 | Kypp | 252/49.6 |
| 3,136,808 | 6/1964 | Emrick | 252/49.6 |
| 4,370,248 | 1/1983 | Horodysky et al. | 252/49.6 |
| 4,410,438 | 10/1983 | Horodysky | 252/49.6 |

Primary Examiner—Jacqueline V. Howard
Attorney, Agent, or Firm—Alexander J. McKillop; Michael G. Gilman; Howard M. Flournoy

[57] ABSTRACT

Borate esters of hydrolyzed hydrocarbyl alkoxides are effective friction modifiers which also provide effective multifunctional properties for lubricants when incorporated therein.

21 Claims, No Drawings

BORATED FRICTION REDUCING ADDITIVES AND COMPOSITIONS THEREOF

BACKGROUND OF THE INVENTION

1. Field of the Invention

This invention relates to lubricant additives and compositions thereof and more particularly to compositions comprising a major proportion of an oil of lubricating viscosity or a grease prepared therefrom containing a minor effective amount of a multifunctional additive consisting of borate esters of hydrolyzed hydrocarbyl alkoxides. Further, this invention relates to the described additives incorporated into lube oils in effective friction-reducing amounts.

2. Description of the Prior Art

It is well known that lubricants by definition reduce friction between moving surfaces; however, friction-reducing additives are agents which, when added to lubricants in minor amounts, significantly enhance the frictional or lubricity properties of those lubricants without modifying their other physical properties such as viscosity, density, pour point and the like.

Alcohols, for example, have long been known for their lubricity properties when formulated into lubricating oils and for their water scavenging characteristics when incorporated into fuel formulations. Hydrocarbon soluble epoxidized fatty acid esters prepared by the epoxidation of unsaturated carboxylic acid esters are also known to have been used as anti-wear and anti-friction additives in lubricants as described in U.S. Pat. No. 4,244,829. Borated hydrolysis products of 1-(2-hydroxyalkyl)-2-alkyl or alkenylimidazolines are known to be effective friction modifying additives as described in U.S. Pat. No. 4,273,665. Further, the use of vicinal hydroxyl containing alkyl carboxylates such as glycerol monooleate have also found widespread use as lubricity additives.

U.S. Pat. No. 4,410,438 to Horodysky discloses borated epoxide additives and lubricants prepared therefrom. In preparation of the additives, an epoxide is reacted with boric acid, boron oxide or an alkyl borate in the absence of added water.

It has now been found that borate esters of hydrolyzed hydrocarbyl alkoxides can significantly reduce friction of lubricants and add a new dimension of antioxidation and high temperature properties to lubricant compositions. The borate esters described herein also possess improved solubility characteristics over those of non-borated derivatives, especially in synthetic fuels. Additionally, these novel additives are non-corrosive to copper and possess anti-wear properties and the ability to provide anti-fatigue characteristics to lubricants or greases containing same.

SUMMARY OF THE INVENTION

The additive compounds useful in this invention are long-chain hydrocarbyl terminal epoxides which have been hydrolyzed using boric acid catalysis and borated to form a mixture of borate esters of the corresponding diols and borate esters of oligomers of the alkyl epoxides which polymerize during hydrolysis. The additive compounds formed in this way are very different from, and often superior to, borate esters, formed by boration of the corresponding preformed diols made by traditional hydrolysis of the described long-chain alkyl epoxides. This invention also includes a novel process to make these boronated esters via boric acid catalysis and boronation to form the disclosed mixture of esters of the diols along with borate esters of oligomers of the epoxides which polymerize during boric acid catalysis. The alkyl groups of the long-chain alkyl epoxides contain at least 14 carbon atoms and up to 36 or more carbon atoms. The epoxide group can be anywhere along the chain, but preferably in the 1,2 or terminal position. The hydrocarbyl epoxides can be straight chain, or branched chain or contain cyclic groups or unsaturated groups, but is preferably saturated alkyl. Preferred epoxides include 1,2-epoxynonadecane, 1,2-epoxyheptadecane, 1,2-epoxytetradecane, 1,3-epoxyhexadecane, 1,2-epoxypentadecane, 1,2-epoxyoctadecane and the like, and mixtures of similar epoxides.

Lubricant compositions comprising oils of lubricating viscosity and greases prepared therefrom containing these novel additives possess multi-functional characteristics. Further, when moving surfaces of, for example, internal combustion engines, are treated with lubricant compositions containing these novel additives, a means or method of obtaining improved fuel economy for said engines is provided.

The amount of additive in the lubricant compositions may range from 0.1 to about 10% by weight of the total lubricant composition. Preferred is from about 0.5 to about 5 wt. %.

The novel compositions embodied herein can, and usually do, include other materials such as corrosion inhibitors, viscosity index improvers, extreme pressure agents, detergents, dispersants, antiwear additives, all of which impart their customary properties to the particular compositions and do not detract from the value of the compositions into which they are incorporated. Such additives often include succinimides, sulfonates, phenates, olefin copolymers, methacylates, zinc dithiophosphates, overbased calcium or magnesium salts and the like. In fact, the disclosed friction reducers often are preferably used with zinc dithiophosphates and in such formulations exhibit significant activity. That is, the novel additives disclosed herein do not prevent these other additives from performing their known purposes, nor are they prevented from performing their purpose by the presence of such other additives. Generally, the total amount of all such materials will not exceed about 10 to 20 wt. %.

The product should contain at least 0.1% boron and may contain 10% or more boron. At least a 5–10% portion of available epoxide groups should preferably be borated. Also, a stoichiometric excess of boronating agent can effectively be used.

The lubricants contemplated for use herein include both mineral and synthetic hydrocarbon oils of lubricating viscosity, mixtures of mineral and synthetic oils, and greases prepared therefrom, and other solid lubricants. The synthetic oils may include polyisobutylenes, hydrogenated olefins, polypropylene glycol, di(2-ethylhexyl) sebacate, dibutyl phthalate, neopentyl esters, pentaerythritol esters, trimethylol propane esters, fluorocarbons, silicate esters, silanes, hydrogenated mineral oils, chain-type polyphenyl, siloxanes and silicaones, and phenoxy phenylethers. Preferred are synthetic formulations. Where the lubricant is to be employed in the form of a grease, the lubricating oil is generally employed in an amount sufficient to balance the total grease composition, after accounting for the desired quantity of the thickening agent and other additive components to be included in the grease formulation. A wide variety of material may be employed as thickening or gelling agents. These may include any of the conventional metal salts or soaps, such as lithium or calcium which are dispersed in the lubricating vehicle in grease-forming quantities in such degree as to impart to the resulting grease composition the desired consistency. Included are lithium or calcium 12-hydroxystearates or stearate soaps or similar metal soaps or non-soap thickeners, such as surface-modified clays and silicas, aryl ureas, calcium complexes and similar materials. In general, grease thickneners may be employed which do not melt and dissolve when used at the required temperature within a particular environment; however, in all other respects, any materials which are normally employed for thickening or gelling hydrocarbon fluids for forming grease can be used in preparing the aforementioned improved grease in accordance with the present invention.

The compounds of this invention may, inter alia, be prepared by reaction of the aforementioned alkoxides with water in the presence of a suitable catalyst, thereafter borated in the presence of a boron-containing reactant and catalyst. The use of more traditional catalysis such as sulfuric acid, hydrochloric acid or p-toluene, sulfonic acid catalysis during this reaction step does not form the same product as is formed by the co-reaction of long-chain epoxide and water and boronating agent. The compounds of this invention are uniquely formed in a one-pot, one-step combined boronation, hydrolysis, polymerization reaction involving the hydrocarbyl epoxides starting materials. No prior art known to applicants describes such compositions, lubricant compositions thereof or the unique process of making such materials. It is not necessary to use the preferred boric acid. Boronating agents such as low-molecular weight trialkyl borates which will form boric acid in the presence of water can also be used. For convenience, however, the boration and hydrolysis may be carried out in a single pot using substantially stoichometric amounts of water. The reaction can be is also carried out in the presence of a solvent having a low boiling temperature such as ethanol or butanol, or other solvent such as toluene or xylene. The reaction time can vary from 2 to about 14 hours. The preferred reaction time is from 4 to about 12 hours. The reaction temperature can vary from about 150° C. to 250° C.

The invention having been described in general terms, the following specific illustrations thereof are offered; however, it is to be understood that they are illustrated only and that the invention is not thereby limited except as by the appended claims.

DESCRIPTION OF SPECIFIC EMBODIMENTS

EXAMPLE 1

Borated, Hydrolyzed, 1,2-Epoxy Mixed $C_{15}$-$C_{18}$ Alkanes

Approximately 245 g of 1,2-epoxy mixed $C_{15}$-$C_{18}$ alkanes obtained commercially and containing approximately the following 1,2-epoxyalkanes - $C_{15}H_{30}O$, 28%; $C_{16}H_{32}O$, 28%; $C_{17}H_{34}O$, 28%; $C_{18}H_{36}H$, 16%; and having an approximate formula weight of 244), 70 g toluene as solvent, 36 g water and 41 g boric acid were charged to a 2 liter stirred reactor equipped with a Dean-Stark condensing trap. Nitrogen was used to blanket the vapor space. The reactor contents were heated up to 100° C. and held for 1½ hours and then heated up to 160° C. over a period of 4 hours and held at 160° C. for 2 additional hours until water evolution, as a result of azeotropic distillation, ceased. The solvent was removed by vacuum distillation and the product was filtered through diatomaceous earth at approximately 100° C. The product formed an off-white waxy solid upon cooling.

EXAMPLE 2

Borated, Hydrolyzed 1,2-Epoxyhexadecane

Approximately 1,000 g of 1,2-epoxyhexadecane, 118 g water, 193 g boric acid and 125 g xylene as solvent were charged to a reactor equipped as described in Example 1. The reactor was heated to 105° C. and held for 12 hours and then the temperature was increased to 225° C. until water evolution, as a result of azeotropic distillation, ceased. The solvent was removed by vacuum distillation and the product was filtered. The product formed an off-white waxy solid upon cooling.

EXAMPLE 3

Borated, Hydrolyzed, 1,2-Epoxyhexadecane

Approxiamately 1,000 g of 1,2-epoxyhexadecane, 118 g water, 258.3 g boric acid and 125 g xylene were charged to a reactor equipped as described in Example 1. The reaction was heated up to 105° C. and held for 12 hours and then the temperature was increased up to 225° C. until water evolution ceased. The solvent was removed by vacuum distillation and the product was filtered to form a clear amber fluid which became an off-white waxy solid upon cooling to room temperature.

The products of the above examples were blended into a fully formulated synthetic automotive engine oil and evaluated using the Low Velocity Friction Apparatus.

EVALUATION OF THE PRODUCTS

Low Velocity Friction Apparatus (LVFA)

The Low Velocity Friction Apparatus (LVFA) is used to measure the friction of test lubricants under various loads, temperatures, and sliding speeds. The LVFA consists of a flat SAE 1020 steel surface (diam. 1.5 in.) which is attached to a drive shaft and rotated over a stationary, raised narrow ringed SAE 1020 steen surface (area 0.08 in²). Both surfaces are submerged in the test lubricant. Friction between the steel surfaces is measured as a function of the sliding spped at a lubricant temperature of 250° F. The friction between the rubbing surfaces is measured using a torque arm strain guage system. The strain guage output, which is calibrated to be equal to the coefficient of friction, is fed to the Y axis of an X-Y plotter. The speed signal from the tachometer-generator is fed to the X-axis. To minimize external friction, the piston is supported by an air bearing. The normal force loading the rubbing surfaces is regulated by air pressure of the bottom of the piston. The drive system consists of an infinitely variable-speed hydraulic transmission driven by a 1½ HP electric motor. To vary the sliding speed, the output speed of the transmission is regulated by a lever-cam-motor arrangement.

Procedure

The rubbing surfaces and 12–13 ml of test lubricant are placed on the LVFA. A 500 psi load is applied, and the sliding speed is maintained at 30 fpm at ambient temperature for a few minutes. A plot of coefficients of friction ($U_k$) over a range of sliding speeds, 5 to 40 fpm (25-195 rpm), is obtained. A minimum of three measurements is obtained for each test lubricant. Then, the test lubricant and specimens are heated to 250° F., another set of measurements is obtained, and the system is run for 50 minutes at 250° F., 500 psi, and 40 fpm sliding speed. Freshly polished steel specimens are used for each run. The surface of the steel is parallel ground to 4 to 8 microinches. The percentages by weight are percentages by weight of the total lubricating oil composition, including the usual additive package. The date are percent decrease in friction according to:

$$\frac{(U_k \text{ of oil alone}) - (U_k \text{ of oil plus additive})}{(U_k \text{ of oil alone})} \times 100$$

Thus, the value for the oil alone would be zero for the form of the data used in the Table below.

TABLE 1

Friction Test Results Using Low Velocity Friction Apparatus

| | Additive Conc. in Base Blend | % Reduction in Coefficient of Friction in LVFA at | |
|---|---|---|---|
| | | 5 Ft./Min. | 30 Ft./Min. |
| Base Blend (fully formulated SAE 5W/30 synthetic engine oil containing detergent/dispersant/inhibitor package) | — | 0 | 0 |
| Example 1 | | | |
| Borated, hydrolyzed, 1,2-epoxy mixed $C_{15}$—$C_{18}$ alkanes | 1 | 24 | 21 |
| Example 2 | | | |
| Borated, hydrolyzed, 1,2-epoxy-hexadecane | 1 | 40 | 30 |
| | 0.5 | 38 | 33 |
| Example 3 | | | |
| Borated, hydrolyzed, 1,2-epoxy-hexadecane | 1 | 24 | 16 |
| | 0.5 | 30 | 18 |

From the data in the above table, it is readily apparent that the subject additive compound significantly improves the friction-reducing properties of lubricants into which they are incorporated. For example, an almost 40% reduction in friction was achieved with the use of only 0.5% of Example 2.

The oxidation stability of the additives was also measured by evaluating the additive blends in 200 second solvent paraffinic neutral lubricating oil using the Catalytic Oxidation Test at 325° F. for 40 hours. The test lubricant composition is subjected to a stream of air which is bubbled through the composition at a rate of 5 liters per hour at 325° F. for 40 hours. Present in the composition are metals commonly used as materials of engine construction; namely (a) 15.6 sq. in. of sand-blasted iron wire
(b) 0.78 sq. in. of polished copper wire
(c) 0.87 sq. in. of polished aluminum wire; and
(d) 0.167 sq. in. of polished lead surface.

Inhibitors for anti-oxidants for the oil are rated on the basis of prevention of oil-deterioration as measured by the increase in acid formation or neutralization number (NN) and kinematic viscosity (KV). The results of the test are reported in Table 2.

TABLE 2

Oxidation Characteristics
Catalytic Oxidation Test, 40 Hours @ 325° F.

| | Additive Conc. Wt. % | % Increase in Viscosity of Oxidized Oil Using KV @ 100° C. | Neut. Number NN | Lead Loss, mg |
|---|---|---|---|---|
| Example | | | | |
| Base Oil (200 second solvent paraffinic neutral lubricating oil) | — | 67 | 3.62 | −1.2 |
| Example 1 | | | | |
| Borated, hydrolyzed, 1,2-epoxy mixed $C_{15}$-$C_{18}$ alkanes | 1 | 17 | 2.08 | 0.0 |
| | 0.5 | 19 | 2.03 | 0.0 |

The results disclosed by the data in Table 2 clearly show the stability exhibited by these multi-purpose friction reducers in the presence of catalytic metals under severe oxidizing conditions at elevated temperatures.

Example 1 was further subjected to the Copper Strip Corrosivity Test. The test was run in 200 second, solvent paraffinic neutral lubricating oil in accordance with ASTM D-130-80. The results disclosed in Table 3 clearly show the borate esters to be non-corrosive to copper.

TABLE 3

Copper Strip Corrosivity Characteristics

| | Additive Conc. Wt. % | Test Rating | |
|---|---|---|---|
| Example 1 | | ASTM D130-80 3 hrs @ 250° F. | ASTM D130-80 6 hrs @ 210° F. |
| Borated, hydrolyzed, 1,2-epoxy mixed $C_{15}$-$C_{18}$ alkanes | 1 | 1A | 1A |

The data disclosed hereinabove dramatically illustrate that borate esters of boron-catalyzed hydrolyzed hydrocarbyl epoxides and compositions containing same can be used to substantially improve the gasoline fuel economy of already fuel efficient synthetic motor oils, and a variety of other lubricants (including both synthetic and mineral oil based automotive and industrial lubricants and greases). Furthermore, these additives have multi-functional characteristics. In addition to friction reducing properties, they also provide anti-corrosion, anti-oxidation, anti-wear and high temperature properties not generally available in a single lubricant additive.

It is understood by those of ordinary skill in the art that variations of this invention within the scope thereof can be readily made.

We claim:

1. A lubricant composition comprising a major proportion of an oil of lubricating viscosity or a grease prepared therefrom and minor effective proportion of from about 0.1 to about 10 wt. % of a multi-functional additive having friction modifying characteristics selected from the group consisting of borate esters of hydrolyzed, hydrocarbyl alkoxides, or mixtures thereof, where the hydrocarbyl moiety contains from 14 to about 36 carbon atoms.

2. The composition of claim 1 wherein said additive is borated hydrolyzed 1,2-epoxy mixed $C_{15}$-$C_{18}$ alkanes.

3. The composition of claim 2 wherein the additive is borated hydrolyzed 1,2-epoxyhexadecane.

4. The composition of claim 1 wherein said composition comprises an oil of lubricating viscosity.

5. The composition of claim 4 wherein said oil is a mineral or refined petroleum oil.

6. The composition of claim 4 wherein said oil of lubricating viscosity is a synthetic oil.

7. The composition of claim 4 wherein said oil of lubricating viscosity is a mixture of mineral and synthetic oils.

8. The composition of claim 4 wherein the oil of lubricating viscosity is a synthetic oil or mixture thereof.

9. The composition of claim 1 wherein said composition comprises a grease.

10. The composition of claim 1 wherein said composition comprises a grease made from mineral oils, synthetic oils, or mixtures of mineral of synthetic oils.

11. The composition of claim 1 wherein said composition contains from about 0.25 to about 4 wt. % of said additive.

12. A method for reducing fuel consumption in an internal combustion engine by treating the moving surfaces thereof with a lubricant composition comprising a major proportion of an oil of lubricating viscosity or grease prepared therefrom and a minor effective amount of a multi-purpose additive having friction-modifying properties selected from the group consisting of borate esters of hydrolyzed hydrocarbyl alkoxides as described in claim 1.

13. The method of claim 12 wherein said additive is borated hydrolyzed 1,2-epoxy mixed $C_{15}$–$C_{18}$ alkanes.

14. The method of claim 13 wherein the additive is borated hydrolyzed 1,2-epoxyhexadecane.

15. The method of claim 13 wherein the oil of lubricating viscosity is a mineral or synthetic oil or mixtures thereof.

16. The method of claim 15 wherein the oil of lubricating viscosity is a synthetic oil or mixtures thereof.

17. A reaction product comprising a borate ester or mixtures of borate esters of hydrolyzed hydrocarbyl alkoxides, or mixtures of alkoxides obtained by (1) hydrolyzing hydrocarbyl epoxides and (2) borating via boric acid catalysis with substantially stoichiometric amounts of water, with or without a suitable solvent, and at temperatures of from about 150° to about 250° C. to form a mixture of borated esters of the corresponding diols and borate esters of oligomers of the epoxides which polymerize during hydrolysis and where the hydrocarbyl moiety is straight or branched chain, cyclic, unsaturated or saturated alkyl and contains from about 14 to about 36 carbon atoms.

18. The product of claim 17 wherein the hydrocarbylalkoxide is a terminal epoxide.

19. The product of claim 17 obtained by borating hydrolyzed 1,2-epoxy mixed $C_{15}$–$C_{18}$ alkanes.

20. The product of claim 17 obtained by borating hydrolyzed 1,2-epoxyhexadecane.

21. The product of claim 17 wherein the borating material is boric acid.

* * * * *

UNITED STATES PATENT AND TRADEMARK OFFICE
CERTIFICATE OF CORRECTION

PATENT NO. : 4,522,734

DATED : June 11, 1985

INVENTOR(S) : Andrew G. HORODYSKY et al

It is certified that error appears in the above-identified patent and that said Letters Patent is hereby corrected as shown below:

Column 4, Line 59, "1-1/2 HP" should read --1/2 HP--.

Signed and Sealed this

Fourteenth Day of January 1986

[SEAL]

Attest:

Attesting Officer

DONALD J. QUIGG

Commissioner of Patents and Trademarks